(12) United States Patent
Keller

(10) Patent No.: US 7,232,465 B2
(45) Date of Patent: Jun. 19, 2007

(54) KNEE PROSTHESIS

(75) Inventor: Arnold Keller, Kayhude (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 0 days.

(21) Appl. No.: 10/522,139

(22) PCT Filed: Jul. 25, 2003

(86) PCT No.: PCT/EP03/08196

§ 371 (c)(1),
(2), (4) Date: Jan. 24, 2005

(87) PCT Pub. No.: WO2004/012633

PCT Pub. Date: Feb. 12, 2004

(65) Prior Publication Data

US 2005/0246029 A1    Nov. 3, 2005

(30) Foreign Application Priority Data

Jul. 26, 2002    (EP) .................................. 02016768

(51) Int. Cl.
*A61F 3/38* (2006.01)
(52) U.S. Cl. .................. 623/20.24; 623/20.31
(58) Field of Classification Search ............ 623/20.21, 623/20.22, 20.23, 20.24, 20.25, 20.26, 20.27, 623/20.28, 20.29, 20.31, 20.3
See application file for complete search history.

(56) References Cited

U.S. PATENT DOCUMENTS

| | | | | |
|---|---|---|---|---|
| 3,868,730 A | * | 3/1975 | Kaufer et al. ............ | 623/20.22 |
| 4,094,017 A | * | 6/1978 | Matthews et al. ........ | 623/20.22 |
| 4,224,697 A | * | 9/1980 | Murray et al. ........... | 623/20.25 |
| 4,950,297 A | * | 8/1990 | Elloy et al. .............. | 623/20.29 |
| 6,117,175 A | * | 9/2000 | Bosredon .................. | 623/20.15 |
| 6,558,427 B2 | * | 5/2003 | Leclercq et al. ......... | 623/20.33 |
| 2005/0107886 A1 | * | 5/2005 | Crabtree et al. ......... | 623/20.24 |

FOREIGN PATENT DOCUMENTS

| DE | 26 60 623 C2 | 8/1976 |
|---|---|---|
| DE | 29 01 009 A1 | 1/1979 |
| DE | 41 02 509 A1 | 1/1991 |
| EP | 0 174 531 A2 | 8/1985 |
| EP | 0 420 460 A1 | 9/1990 |
| WO | WO 200113825 A1 * | 3/2001 |

OTHER PUBLICATIONS

English translation of International Preliminary Examination Report issued in counterpart PCT/EP2003/008196.

* cited by examiner

*Primary Examiner*—Corrine McDermott
*Assistant Examiner*—Thomas J. Sweet
(74) *Attorney, Agent, or Firm*—Morrison & Foerster LLP

(57) ABSTRACT

A knee prosthesis includes a femoral prosthetic part which forms a pair of condylar gliding surfaces, a tibial part that has tibial gliding surfaces cooperating with the condylar gliding surfaces and a coupling part that connects the femoral and tibial parts so that they can rotate about a rotational axis that is approximately parallel to the axis of the tibia. If the femoral and tibial parts have the same anteroposterior alignment, an applied load is borne by a central region of the tibial gliding surfaces. The tibial gliding surface slopes upwardly relative to the prosthesis both in front of and behind the central region of the tibial gliding surface so that when the femoral and tibial parts rotate against one another, each of the condylar gliding surfaces remains in contact with its corresponding tibial gliding surface.

4 Claims, 2 Drawing Sheets

KNEE PROSTHESIS

BACKGROUND OF THE INVENTION

To replace the human knee joint, prosthesis types are used whose femoral and tibial parts, depending on the state of preservation of the ligament apparatus, are guided relative to one another with a greater or lesser degree of constraint. This concerns the main degrees of freedom of movement of the knee, namely the flexion movement about a transverse axis, the rotation movement about a rotation axis running approximately parallel to the direction of the tibia, and a translation movement in the anteroposterior direction. The least degree of mutual constrained guidance is to be found in what are called uncoupled prostheses, which are made up simply of a pair of femoral condyles and of a tibial sliding surface. They are used in cases where the ligament apparatus is well preserved. The other extreme is constituted by hinge prostheses, which are used in cases of poorly preserved ligament apparatus and which restrict the possible movements of the knee to the flexion movement (EP-A-42 04 60, DE-OS-29 01 009). Between these extremes there are varying degrees of partially coupled systems comprising, between the femoral part and the tibial part, an intermediate part which, by forming a rotation bearing, takes over the guidance functions for the rotation movement.

Among the partially coupled prostheses which permit a rotation movement, two types are to be distinguished. In the first type, the entire load is transmitted via the intermediate joint component which, in relation to the tibial part, forms a rotation bearing, and, in relation to the femoral part, forms a flexion hinge joint (DE-C-26 60 623). Since in this case the condylar sliding surfaces are intended only for a flexion movement, they can be designed congruent with the opposite surfaces. The opposite surfaces are therefore made concave with the same radius of curvature. The second type of partially coupled prostheses transmits the load not via the intermediate joint component, but directly from the condylar sliding surfaces to tibial sliding surfaces cooperating with these (EP-A-174 531). In this case, not only does a flexion movement take place between the condylar sliding surfaces and the tibial sliding surfaces, but also the rotation movement. For this reason, the tibial sliding surfaces should not be made congruent with the condylar sliding surfaces. If they are to permit a free rotation movement, the tibial sliding surfaces have to be flat. In general, however, they are allowed to slope slightly upward in front of the area in which they cooperate with the condylar surfaces when the femoral part and the tibial part have the same anteroposterior alignment (area of normal contact). This has the effect that, in the event of rotation, the condylar sliding surface displaced forward in relation to the tibial sliding surface during the rotation is lifted. This generates, under the load transmitted from the joint, a restoring torque which ensures that the prosthesis parts, as soon as is possible, return to their normal position of having the same anteroposterior alignment. During the rotation relative to the tibial part and the thereby obtained lifting of the femoral part, the rearwardly migrating condylar surface loses its contact with the tibial sliding surface. The entire load then has to be transmitted on the other side, which leads not just to increased wear, but also to an undesired bending moment in the area of the rotation bearing. It is from this prior art that the invention starts out.

In a known publication (DE-A-41 02 509), a partially coupled prosthesis is discussed in which both the flexion movement and also the rotation movement takes place between the femoral and tibial sliding surfaces. The femoral sliding surfaces are rounded convexly in the sagittal and frontal plane. From the view of the tibial sliding surfaces, it can be concluded that they are identical to and complement the shape of the femoral sliding surfaces. This permits a rotation movement of the knee components relative to one another about the flexion axis, but provides high resistance to a rotation moment about the axis parallel to the direction of the tibia. The known prosthesis is therefore not suitable for such a rotation movement. Were such a rotation to take place, however, the femoral sliding surfaces would spring out of the tibial slide depressions and there would no longer be any stability of the prosthesis against further rotation. In addition, the femoral sliding surfaces would lie only on the edges of the tibial slide depressions and deform these under load. The publication provides no information on how the sliding surfaces have to be configured so that they ensure both the possibility of rotation and also stability upon rotation and so that, in the event of rotation, force can be transmitted in a way that does not damage the prosthesis.

SUMMARY OF THE INVENTION

Starting out from the prior art as indicated above, the object of the invention is to improve force transmission between the prosthesis components in the event of rotation about the longitudinal axis of the tibia. The solution lies in the features of the invention as disclosed herein.

Accordingly, the tibial sliding surfaces also slope upward behind the areas of normal contact, specifically in such a way that, in the event of rotation, each of the two condylar sliding surfaces remains touching the associated tibial sliding surface; one condylar sliding surface is in contact with the upwardly sloping part of the tibial sliding surface in front of the area of normal contact, the other with the area sloping upward to the rear.

The application of this principle is advantageous in knee prostheses with a rotation axis which is fixed in relation to both prosthesis parts, in other words in which no anteroposterior movement of the prosthesis parts in relation to one another can take place. The upward slope of the tibial sliding surfaces behind the area of normal contact is then roughly the same as that in front of this area. The invention, however, can also be used in prostheses whose rotation axis is displaceable in the anteroposterior direction in relation to one of the two prosthesis parts. The condylar sliding surfaces then position themselves relative to the tibial sliding surfaces in the antero-posterior direction in such a way that the force transmission conditions on both condyles compensate each other.

The geometric relationships are particularly simple and clear when the radius of curvature of that part of the condylar sliding surfaces cooperating with the tibial sliding surface is substantially constant in the flexion plane, i.e. when the condylar sliding surfaces are configured as arcs of a circle. The invention, however, can also be used when this is not the case. If the course of the condylar surfaces is irregular, it is nevertheless expedient to provide for relative movement of the femoral and tibial parts in the anteroposterior direction. This is not necessary when the condylar sliding surfaces are shaped in the manner of an Archimedes spiral. The profile of the condylar sliding surfaces should generally be constant.

BRIEF DESCRIPTION OF THE DRAWINGS

The invention is explained in more detail below with reference to the drawing which depicts an advantageous illustrative embodiment and in which.

DETAILED DESCRIPTION OF THE INVENTION

Figure 1:
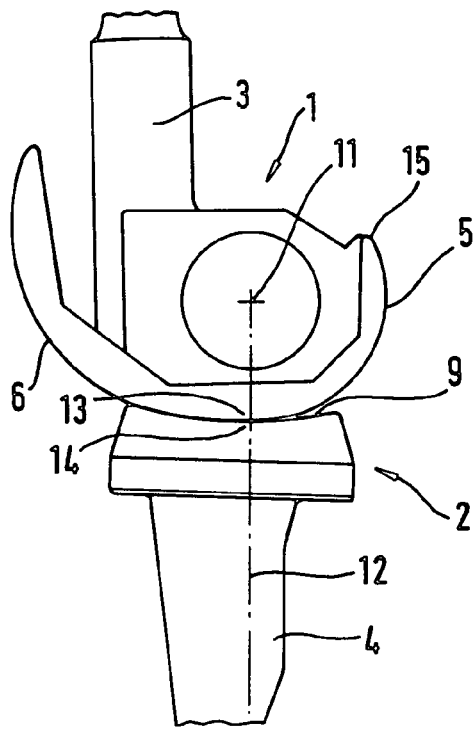
FIG. 1 shows a side view of the prosthesis.
Figure 2:
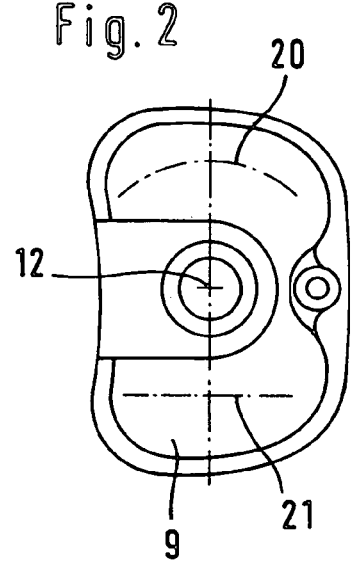
FIG. 2 shows a plan view of the tibial sliding surfaces.

The prosthesis has a femoral part 1 and a tibial part 2 which, in a known manner, are to be anchored via pins 3, 4 respectively at the lower end of the femur and at the upper end of the tibia. The femoral part 1 has a pair of condylar sliding surfaces 5 which, at the front, come together to form a patellar sliding surface 6. The tibial part 2 forms, at the top, a support plate 7 on which the so-called tibial plateau 8 made of a material promoting sliding, for example polyethylene, is anchored, said tibial plateau 8 forming the tibial sliding surfaces 9 on which the condylar sliding surfaces 5, preferably made of polished metal, slide. The femoral part 1 and the tibial part 2 are coupled to one another by an intermediate part 10 which on the one hand, with the femoral part 1, forms a flexion bearing with axis 11, and, on the other hand, with the tibial part, forms a rotation bearing with axis 12. Details of this construction are explained in European patent applications 1,110,261 and 1,111,551, to which reference is hereby made and whose disclosure is made part of the subject of the present application.

Figure 6:
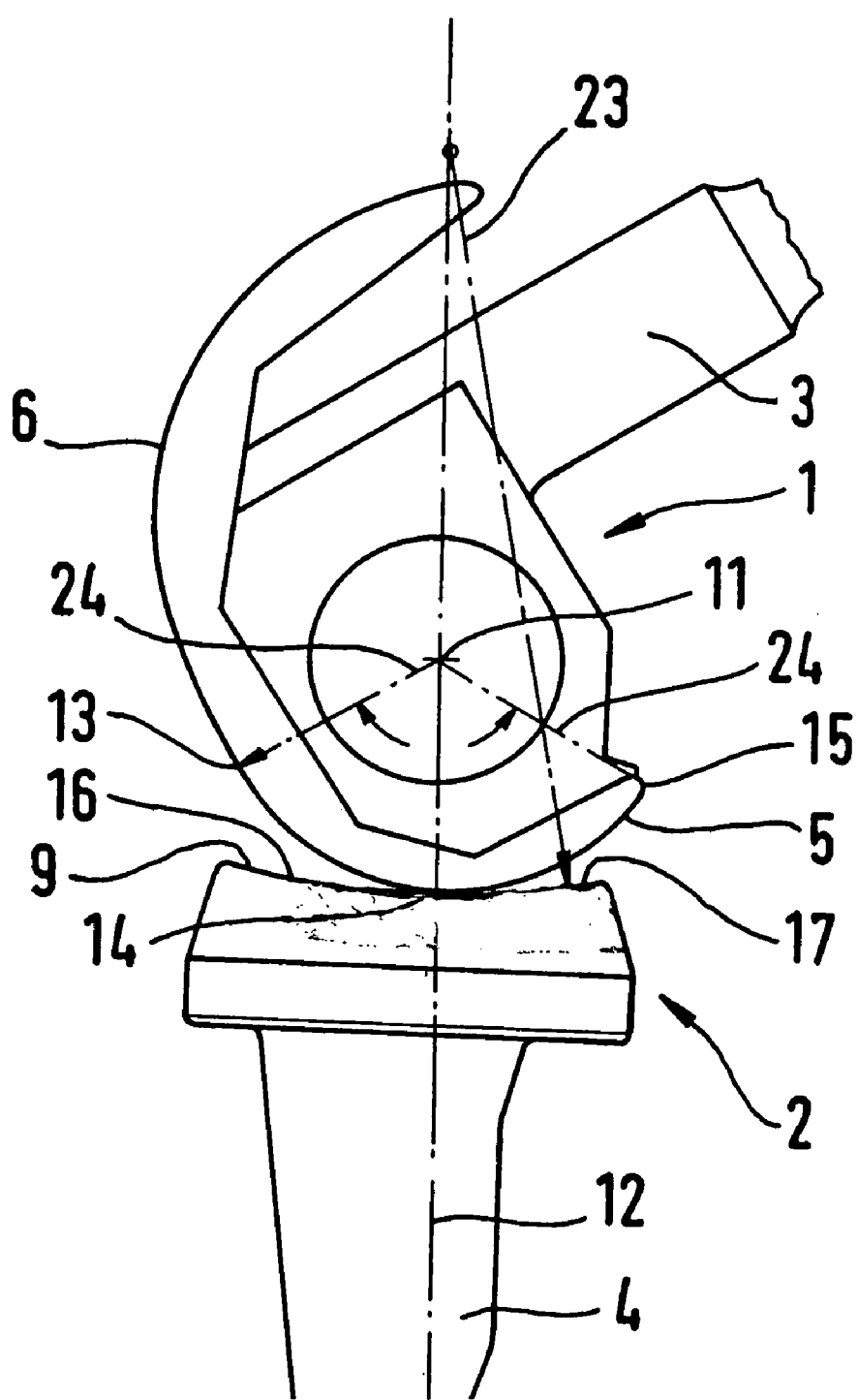
FIG. 6 shows a side view of the prosthesis in flexure.

In the non-rotated position (FIG. 1), the femoral sliding surfaces 5 rest with their area 13, whose direction runs approximately perpendicular to the radius, on the area 14 of normal contact of the tibial sliding surfaces 9, the direction of which area 14 runs approximately perpendicular to the axis 12. Upon flexion movement (FIG. 6), the portion lying between the area 13 and the rear end 15 of the femoral sliding surfaces can come into contact with the tibial sliding surface 9. In the example shown, this portion extends as an arc of a circle of constant radius 24 to the flexion axis 11. The profile of the sliding surface is constant in this portion.

The area 14 of the tibial sliding surface 9 has the same profile (in frontal section) as that portion 13-15 of the associated femoral sliding surface cooperating with it. This means that, in the non-rotated state, theoretical linear contact exists. In practical terms, surface contact is obtained as a result of the compliance of the material of the tibial sliding surfaces 9.

That portion 6 of the condylar sliding surfaces and of the patellar sliding surface lying in front of the area 13 is not of importance as regards the transmission of the load forces to the tibial part 2 of the prosthesis.

Figure 3:
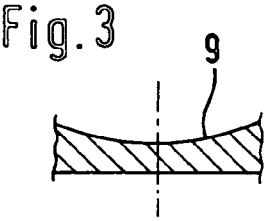
FIG. 3 shows a section through the tibial slid-in surfaces taken along line 21 of FIG. 2, and FIGS. 4 and 5 show two side views from opposite sides, with the femoral part rotated.
Figure 4:
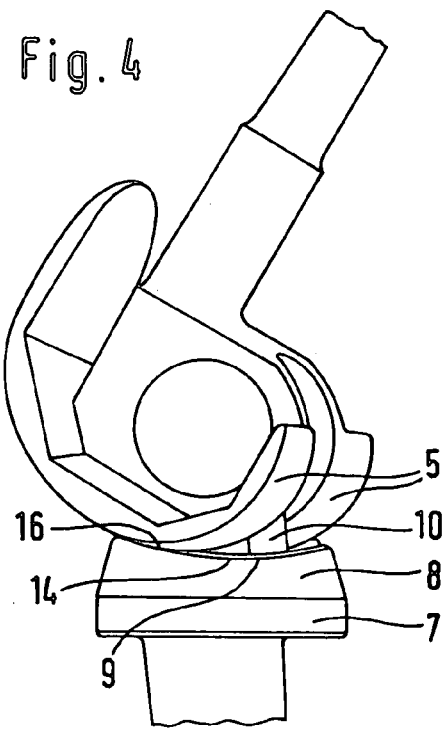
Figure 5:
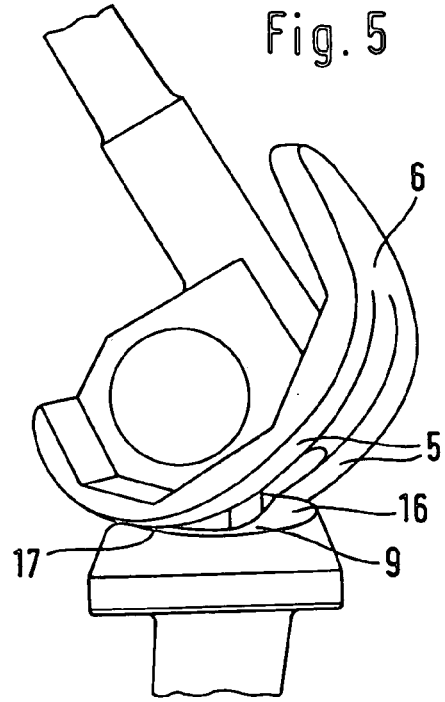

The tibial sliding surface 9 is weakly concave in the sagittal plane, as is shown in FIG. 3. The radius 23 of curvature is considerably greater than the radius of the femoral sliding surface portion 13-15. This is necessary so that, in the event of rotation, the femoral sliding surfaces can move forward and backward a slight distance—substantially without impediment—starting from the area of normal contact 14. In the event of powerful rotation, the condylar sliding surfaces 5 leave the area 14 of normal contact. On one side (see FIG. 4), they move in the upwardly sloping portion 16 of the tibial sliding surfaces which lies in front of the area of normal contact 14. On the other side (FIG. 5), they move in the rear, upwardly sloping portion 17 of the tibial sliding surfaces 9.

The tibial sliding surfaces are shaped in such a way that, in the event of such rotation, the condylar sliding surfaces 5 maintain contact with the tibial sliding surface 9 on both sides, namely, on one side with the front portion 16, and, on the other side, with the rear portion 17.

If one wishes to maintain linear contact between the condylar sliding surfaces 5 and the tibial sliding surfaces 9 in these portions, then the tibial sliding surfaces 9 have to be shaped such that they have the same profile as the condylar sliding surfaces 5 in the direction of circle arcs 20 about the rotation axis 12 in a sectional plane containing this rotation axis. This can readily be achieved with the aid of a tool which has the profile of the condylar sliding surfaces and is rotated about the axis 12. However, this is relatively complicated. It is simpler to mill the tibial sliding surfaces 9 by means of tools that are moved in the anteroposterior direction. In this case, when rotation takes place, the ideal linear contact between the condylar sliding surfaces 5 and the tibial sliding surfaces 9 is dispensed with to a greater extent the farther the point of the respective contact is removed from the area 14 of normal contact. This is not a problem, however, because such strong rotation occurs relatively rarely and the periods of sustained load transmission to the area 14 of normal contact are limited. In the event of such strong rotation, it is crucial that not just one of the two condylar sliding surfaces cooperates with the tibial sliding surface, but both.

The invention claimed is:

1. A knee prosthesis, comprising a femoral prosthetic part which forms a pair of condylar sliding surfaces, a tibial part which has tibial sliding surfaces configured for cooperating with and rotating relative to the condylar sliding surfaces, and a coupling part which connects the femoral and tibial parts so that they rotate about a rotation axis approximately parallel to a tibial shaft when implanted, wherein the tibial sliding surfaces having areas of normal contact which, when the femoral and tibial parts have the same anteroposterior alignment, cooperate with corresponding condylar sliding surfaces, and wherein the tibial sliding surfaces have first further areas in front of the areas of normal contact sloping upward with a radius of curvature greater than the radius of curvature of the portion of the corresponding condylar sliding surface cooperating during flexion with the tibial sliding surface and second further areas sloping upward behind the areas of normal contact, the first and second further areas being configured relative to the areas of normal contact in such a way that, in the event of rotation of the tibial part of the prosthesis relative to the femoral part about the rotation axis when implanted, each of the condylar sliding surfaces remains in load-transmitting contact with the first or second further area of its corresponding associated tibial sliding surface during the rotation.

2. The prosthesis as claimed in claim 1, wherein the rotation axis is fixed in relation to the femoral and tibial prosthesis parts in an anteroposterior direction.

3. The prosthesis as claimed in claim 1, wherein a portion of the condylar sliding surface corresponding to the tibial sliding surface has a radius of curvature that is substantially constant in a flexion plane.

4. The prosthesis as claimed in claim 2, wherein a portion of the condylar sliding surface corresponding to the tibial sliding surface has a radius of curvature that is substantially constant in a flexion plane.

* * * * *